(12) United States Patent
Jamison et al.

(10) Patent No.: US 10,241,019 B2
(45) Date of Patent: Mar. 26, 2019

(54) VARIABLE DIAMETER VISCOMETER FOR EVALUATING WELL FLUIDS

(71) Applicant: Halliburton Energy Services, Inc., Houston, TX (US)

(72) Inventors: Dale E. Jamison, Humble, TX (US); Kenneth Heidt Matthews, Kingwood, TX (US); Andrew David Vos, Spring, TX (US)

(73) Assignee: Halliburton Energy Services, Inc., Houston, TX (US)

( * ) Notice: Subject to any disclaimer, the term of this patent is extended or adjusted under 35 U.S.C. 154(b) by 130 days.

(21) Appl. No.: 15/322,812

(22) PCT Filed: Jul. 31, 2014

(86) PCT No.: PCT/US2014/049273
§ 371 (c)(1),
(2) Date: Dec. 29, 2016

(87) PCT Pub. No.: WO2016/018405
PCT Pub. Date: Feb. 4, 2016

(65) Prior Publication Data
US 2017/0176310 A1 Jun. 22, 2017

(51) Int. Cl.
*G01N 11/14* (2006.01)
*G01N 11/00* (2006.01)

(52) U.S. Cl.
CPC ...... *G01N 11/14* (2013.01); *G01N 2011/0006* (2013.01)

(58) Field of Classification Search
CPC .......................... G01N 11/14; G01N 2011/0006
See application file for complete search history.

(56) References Cited

U.S. PATENT DOCUMENTS 3,270,553 A * 9/1966 Ballman ................ G01N 11/08
425/398
4,185,493 A * 1/1980 Frosch ................... G01N 11/04
264/40.4
(Continued)

FOREIGN PATENT DOCUMENTS

SU          696349      * 11/1979  ............. G01N 11/14
WO      2013001538 A1     1/2013
WO      2016018405 A1     2/2016

OTHER PUBLICATIONS

Bacher, M., et al., "Snow Experiments with a large-scale coaxial rheometer," CemOA: Archive ouverte d'Irstea/Cemagref, European Geosciences Union general assembly, Vienna, AUT, Apr. 15-20, 2007, 1 page, CemOA publications.

*Primary Examiner* — John Fitzgerald
(74) *Attorney, Agent, or Firm* — Tenley Krueger; Parker Justiss, P.C.

(57) ABSTRACT

Some examples of a variable diameter viscometer for evaluating well fluids can be implemented to perform a method. A well fluid including solid well particles is received in a gap formed between a first portion and a second portion of the viscometer. A width of the gap is adjustable during operation of the viscometer. Rheological properties of the fluid are evaluated by applying a shear to the well fluid in the gap by moving the first portion and the second portion relative to each other, and adjusting the width of the gap between the first portion and the second portion based, at least in part, on a size distribution of the solid well particles in the well fluid.

20 Claims, 6 Drawing Sheets

(56) References Cited

U.S. PATENT DOCUMENTS

| | | | |
|---|---|---|---|
| 5,277,058 A | 1/1994 | Kalyon et al. | |
| 5,316,261 A | 5/1994 | Stoner | |
| 5,610,325 A * | 3/1997 | Rajagopal | G01N 11/142 73/54.35 |
| 6,497,678 B2 | 12/2002 | Schock | |
| 6,499,336 B1 * | 12/2002 | Raffer | G01N 11/14 73/54.23 |
| 7,434,981 B2 * | 10/2008 | Amasaki | C09C 1/646 241/23 |
| 8,020,432 B1 * | 9/2011 | Ballato | G01N 11/16 73/54.39 |
| 8,266,949 B2 * | 9/2012 | Harris | G01N 11/10 73/54.28 |
| 8,499,619 B2 | 8/2013 | Raffer | |
| 8,904,852 B2 * | 12/2014 | Wollny | G01N 11/142 73/54.01 |
| 2001/0037687 A1 | 11/2001 | Brovold et al. | |
| 2001/0042400 A1 * | 11/2001 | Boyle | B03C 3/28 73/54.28 |
| 2003/0154772 A1 | 8/2003 | Jackson | |
| 2010/0170327 A1 | 7/2010 | Glauner et al. | |
| 2011/0030454 A1 * | 2/2011 | Laun | G01N 11/14 73/54.28 |
| 2011/0061451 A1 * | 3/2011 | Harris | G01N 11/10 73/54.42 |
| 2012/0024047 A1 * | 2/2012 | Wollny | G01N 11/142 73/54.42 |
| 2012/0081707 A1 | 4/2012 | Norden | |
| 2013/0118235 A1 * | 5/2013 | Morgan | G01N 11/14 73/54.28 |
| 2016/0349163 A1 * | 12/2016 | Chen | G01N 11/14 |

* cited by examiner

VARIABLE DIAMETER VISCOMETER FOR EVALUATING WELL FLUIDS

CROSS-REFERENCE TO RELATED APPLICATION

This application is the National Stage of, and therefore claims the benefit of, International Application No. PCT/US2014/049273 filed on Jul. 31, 2014, entitled "VARIABLE DIAMETER VISCOMETER FOR EVALUATING WELL FLUIDS," which was published in English under International Publication Number WO 2016/018405 on Feb. 4, 2016. The above application is commonly assigned with this National Stage application and is incorporated herein by reference in its entirety.

TECHNICAL FIELD

This disclosure relates to evaluating well fluids, e.g., drilling fluids, production fluids, or other well fluids.

BACKGROUND

Viscometers are used to measure rheological properties, e.g., viscosity, flow parameters, or other rheological properties, of fluids. A Couette viscometer can be operated to determine fluid viscosity based on a force required to turn an object in the fluid. Such a viscometer includes two co-axial cylinders (i.e., an inner cylinder and an outer cylinder) with a gap in between. A volume of the fluid to be tested is flowed in the gap and the two cylinders are rotated relative to each other. For example, the outer cylinder can be rotated at a predetermined speed while the inner cylinder is held stationary (or vice versa). The viscometer can measure the shear stress on the fluid as the outer cylinder rotates. A ratio of the shear stress to the shear rate, determined from the rotational speed of the outer cylinder, yields the viscosity of the fluid in the gap.

Sometimes, the gap between the two co-axial cylinders may need to be changed, e.g., to evaluate different fluids having different viscosities, to evaluate the same fluid at different shear rates or for other reasons. The gap may also need to be changed when evaluating well fluids, e.g., drilling fluids, production fluids, or other well fluids, that can sometimes include solid particles, e.g., drilling cuttings, pieces of the wellbore formation, or other solid particles, causing well fluid viscosities to be different at the same shear rate. Changing the gap between the two co-axial cylinders may require replacing either the inner cylinder or the outer cylinder or both for each fluid to be evaluated.

DESCRIPTION OF DRAWINGS

Like reference symbols in the various drawings indicate like elements.

DETAILED DESCRIPTION

This disclosure describes a variable diameter viscometer for evaluating well fluids. In general, the viscometer includes a first portion and a second portion that is positioned adjacent to the first portion. The arrangement of the first and second portions results in a gap between the two portions. Rheological properties of fluids can be evaluated by flowing the fluid into the gap and then applying a shear on the fluid by moving the first portion and second portion relative to each other. The gap between the two portions of the viscometer described here can be varied without requiring that either of the two portions be removed or replaced. In some implementations, the gap can be varied during operation of the viscometer, e.g., while the two portions are moving relative to each other. The viscometer can be implemented to evaluate the viscosity of a well fluid that includes solid particles of different sizes. The viscometer can also be implemented to evaluate rheological properties of a continuous stream of fluid. For example, the fluid can continuously be flowed through the gap between the two portions. Different samples of the fluid that flow through the viscometer at different time instants can have different viscosities, e.g., due to the absence or presence of different sizes or volume fractions (or both) of solid particles (or other materials intentionally added or not) in the different samples. The viscometer can be implemented to continuously and in real-time adjust the gap between the two moving portions to determine the different viscosities of the different samples without requiring removal or replacement of one of the portions to adjust the gap to accommodate each sample.

Implementations of the viscometer described here can enable evaluating rheological properties of fluids, e.g., well fluids or other fluids, with a wide range of viscosities without changing the viscometer's torsion spring. In addition, varying the gap in the viscometer can allow applying different shear rates to the fluids while maintaining a constant relative velocity between the two moving portions. For example, slurries with lost circulation material (LCM) that are sometimes too large to be evaluated using field viscometers can be evaluated using the viscometer described here. In another example, the viscometer described here can be implemented with components that can easily be removed from materials such as cements or resins after the materials have completely reacted or set up. In another example implementation, the viscometer can measure the viscosity of cutting laden drilling fluids such as those at a well flow line. The viscometer can be implemented to qualitatively approximate large solids volume content and size with materials such as cuttings, e.g., by coupling sensors, such as strain sensors, LVDT, RVDT, optical, ultrasonic, hall effect or other sensors, with the viscometer. The variable configuration allows the relative size of the two portions and thus capabilities to be changed in environmental conditions where a complete shut-down of an operation may be required for configuration changes in zones such as Class I Div 1. Velocity of one or more members may be varied to provide a shear rate range as well. In this rheometer design, both the gap and the relative velocity may be varied simultaneously to achieve a constant shear rate. In some fluids, this may be used to indicate the degree of shear thinning of the test fluid.

Figure 1:
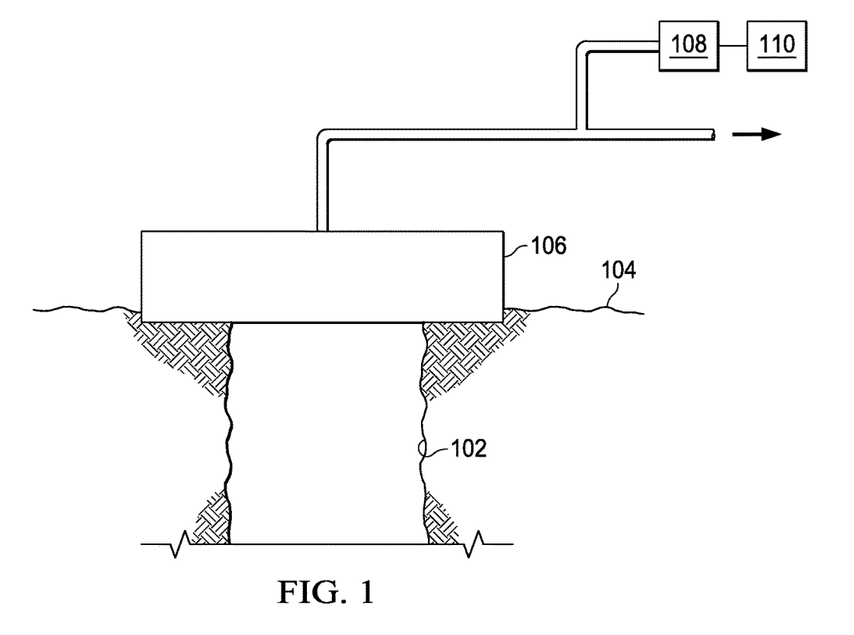
FIG. 1 is a schematic diagram of a well system including a variable diameter viscometer.

FIG. 1 is a schematic diagram of a well system including a variable diameter viscometer. A wellbore 102 is formed in a subterranean zone (e.g., a formation, multiple formations or a portion of a formation). A well head 106 is connected to an entrance of the wellbore 102 at a surface 104. In some implementations, all or portions or none of the wellbore 102 can be cased. Well fluids can flow into and out of the wellbore 102. Example well fluids include drilling fluid, production fluid, cements, resins or other well fluids. For example, when forming the wellbore 102 (or at other times), drilling fluid can be pumped into the wellbore 102 through a tubing, through a drilling system that is positioned in the wellbore 102, and out through an annulus between the tubing and an inner wall of the wellbore 102. The drilling fluid can carry drilling cuttings, e.g., pieces of the wellbore 102 that have been cut during drilling, debris, or other solid materials, to the surface 104. At the surface 104, tubing can be connected to the well head 106 to transport the drilling fluid away from the wellbore 102.

Figure 2A:
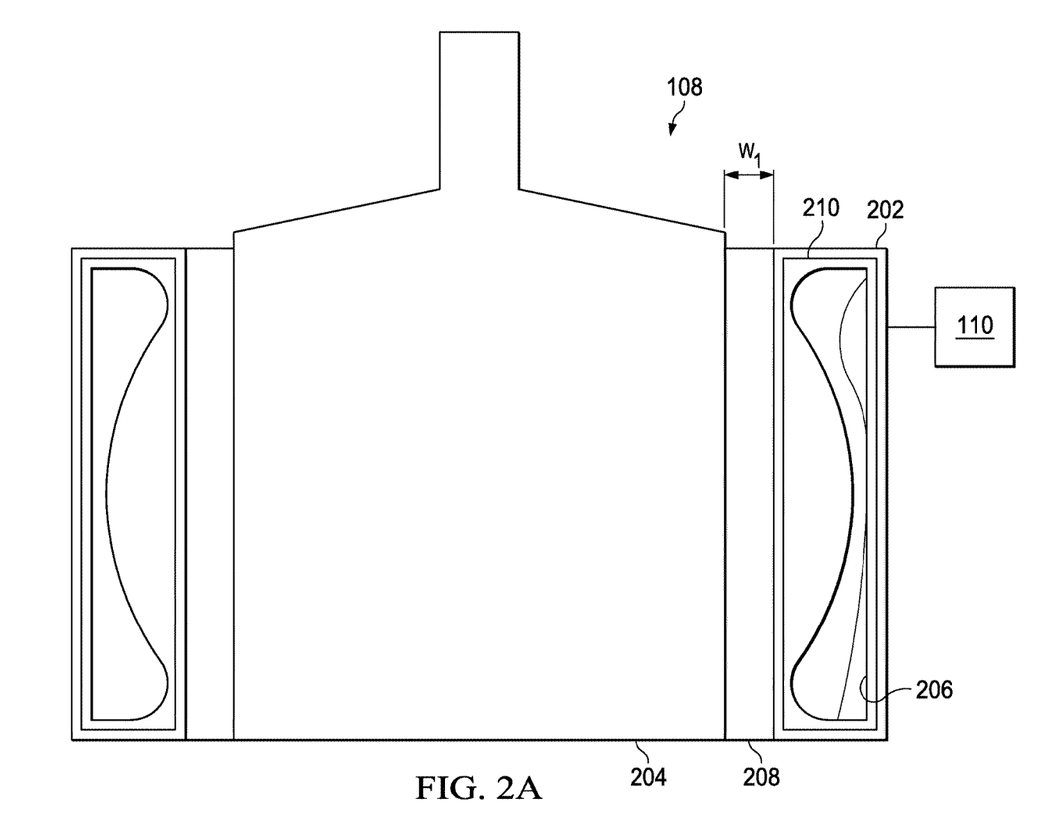
FIGS. 2A and 2B are schematic diagrams of a first implementation of the variable diameter viscometer.
Figure 2B:
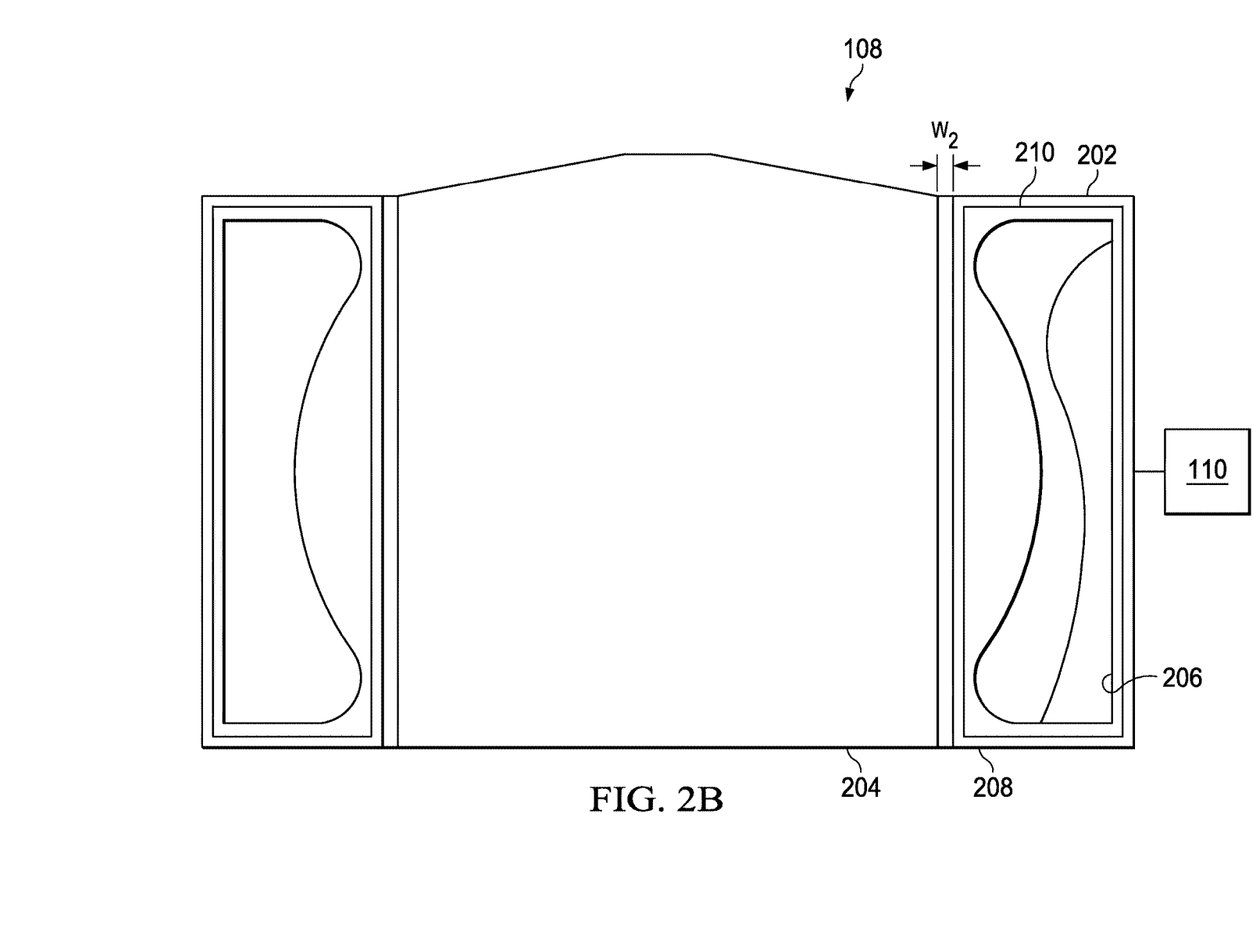

In some implementations, a variable diameter viscometer 108 can be connected, e.g., in series or in parallel, to the tubing that transports the drilling fluid away from the wellbore 102. FIGS. 2A and 2B are schematic diagrams of a first implementation of the variable diameter viscometer 108. In some implementations, the viscometer 108 includes an outer cylinder 202 and an inner cylinder 204 arranged relative to the outer cylinder to form a gap 208. The outer cylinder 202 and the inner cylinder 204 can rotate relative to each other to apply shear to a fluid (e.g., drilling fluid, production fluid, or other fluid) received in the gap 208. For example, the outer cylinder 202 can be rotated and the inner cylinder 204 can be held stationary. In such implementations, the outer cylinder 202 and the inner cylinder 204 can be a rotor and a stator, respectively. Alternatively, the outer cylinder 202 can be a stator (i.e., held stationary) and the inner cylinder 204 can be a rotor (i.e., rotated).

A width of the gap 208 between the outer cylinder 202 and the inner cylinder 204 can be adjusted, i.e., increased by increasing a diameter of the inner cylinder 204 or decreasing a diameter of the outer cylinder 202 or both, and decreased by decreasing the diameter of the inner cylinder 204 or increasing the diameter of the outer cylinder 202 or both. In some implementations, the width of the gap 208 can be adjusted during operation of the viscometer 108, i.e., while the outer cylinder 202 and the inner cylinder 204 are rotating relative to each other. In some implementations, the width of the gap 208 can be adjusted without having to remove or replace either the outer cylinder 202 or the inner cylinder 204. The viscometer 108 can include an inflatable membrane 206 (e.g., a bellow), which, when inflated or deflated, can change the width of the gap 208. In some implementations, a bellows design can be used to change the outer or inner cylinder size. In some implementations, a spiraled material can form a variable cylinder dimension.

In some implementations, the viscometer 108 can be connected to a controller 110 which can adjust the width of the gap 208, e.g., while the inner cylinder 204 and the outer cylinder 202 rotate relative to each other. The controller 110 can be implemented as processing circuitry that includes hardware, software, firmware, or combinations of them. Alternatively or in addition, the controller 110 can be implemented as a computer system that includes a data processing apparatus (e.g., one or more processors) and a computer-readable medium storing instructions executable by the data processing apparatus to perform operations of the controller 110.

For example, the controller 110 can be connected to the inflatable membrane 206 and can control the pressure in the membrane 206 hydraulically, pneumatically, mechanically, a combination of them, or other techniques. FIG. 2A shows the inflatable membrane 206 positioned in the outer cylinder 202, which is arranged relative to the inner cylinder 204 to have a width, $W_1$, for the gap 208. By increasing the pressure in the inflatable membrane 206, the controller 110 can decrease the width of the gap from $W_1$ to $W_2$, as shown in FIG. 2B. Conversely, the controller 110 can increase the width of the gap by decreasing the pressure in the inflatable membrane 206.

In the example schematic diagrams shown in FIGS. 2A and 2B, the inflatable membrane 206 is positioned in the outer cylinder 202. In alternative implementations, an inflatable membrane can be positioned in the inner cylinder 204 or an inflatable membrane can be positioned in each of the inner cylinder 204 and the outer cylinder 202. In some implementations, the inflatable membrane can be positioned in the stationary cylinder while, in others, the membrane can be positioned in the rotating cylinder.

In some implementations, the viscometer 108 can include a calibration sensor 210 that is connected to the inflatable membrane 206 and the controller 110. The controller 110 can operate the calibration sensor 210 to determine a relationship between the width of the gap 208 and the pressure in the inflatable membrane 206. The calibration sensor 210 can be, e.g., a mechanical sensor such as a strain gauge, fluid-based pressure calibration sensor, or other mechanical sensor, an optical sensor or other type of calibration sensor. In an example in which the calibration sensor 210 is a fluid-based pressure calibration sensor, the controller 110 can correlate pressure or fluid volume into the membrane with the width of the gap 208.

In some implementations, the controller 110 can apply a range of pressures to the inflatable membrane 206, and responsively determine a range of respective widths of the gap 208. The controller 110 can store the range of pressures and the range of gaps in a storage medium. To adjust the width of the gap 208 to a specified value, the controller 110 can identify the pressure to be applied to the inflatable membrane 206. A calibration fluid can be used in the rheometer gap to calibrate the shear stress response of the rheometer. A specified rotational rate and gap size will provide an expected shear stress response for a calibration fluid. The pressure required to achieve the expected shear stress response will yield the calibrated pressure required to set the gap size.

Figure 2C:
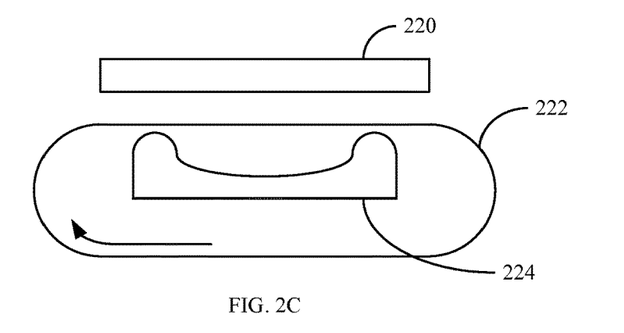
FIGS. 2C and 2D are schematic diagrams of a second implementation of implementation of the variable diameter viscometer.
Figure 2D:
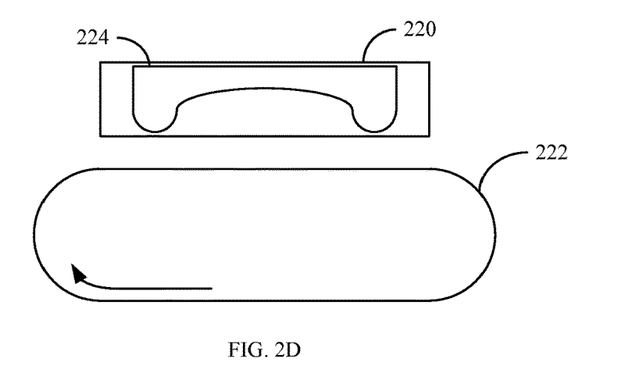

The implementation shown in FIGS. 2A and 2B can be a Couette viscometer that includes two co-axial cylinders. Similar techniques can be applied to other viscometer implementations such as parallel plate viscometers, cone and plate rheometers, or other viscometer implementations. FIGS. 2C and 2D are schematic diagrams of a second implementation of the viscometer. FIG. 2C shows a first portion 220 and a second portion 222 arranged to form a gap in which the well fluid including solid well particles can be received. The first portion 220 can be a stationary plate and the second portion 222 can be a movable plate that can be moved relative to the stationary plate. FIG. 2C shows the inflatable membrane 224 positioned in the second portion 222 while FIG. 2D shows the inflatable membrane 224 positioned in the first portion.

Figure 2E:
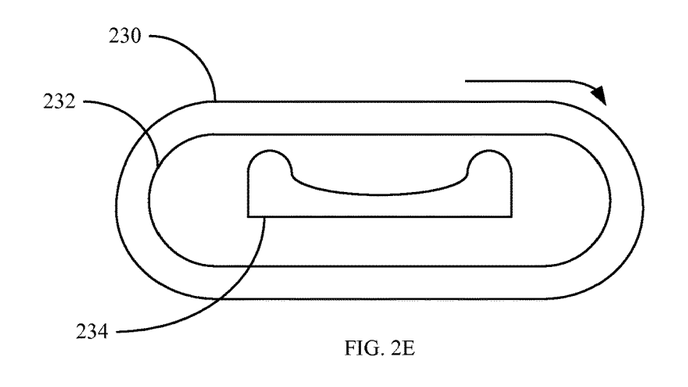
FIG. 2E is a schematic diagram of a third implementation of the variable diameter viscometer.

FIG. 2E is a schematic diagram of a third implementation of the viscometer, and is a variation of the Couette viscometer described with reference to FIGS. 2A and 2B. In this implementation, the first portion 230 and the second portion 232 can be arranged as an outer elliptical portion and an inner elliptical portion, respectively. The first portion 230 can encompass the second portion 232 to form a gap in which the well fluid with the solid well particles is received. Either the first portion 230 or the second portion 232 or both can be rotated to apply a shear on the well fluid. FIG. 2E shows the inflatable membrane 234 positioned in the second portion 232. The membrane 234 can alternatively be positioned in the first portion 230.

Example implementations of the viscometer can be implemented in conjunction with a well system to evaluate rheological properties of well fluids. The viscometer can, alternatively or in addition, be implemented independently of the well system, e.g., as a stand-alone system. For example, the viscometer can be implemented in a laboratory to evaluate rheological properties of any fluid. Also, example implementations are described below with reference to evaluating drilling fluid carrying drilling cuttings using the viscometer. Other well fluids that can be evaluated using the viscometer include production fluids (e.g., oil), cement, slurries, resins, or other well fluids. For example, the viscometer can be implemented to evaluate the resins or the cement slurries as setting occurs to a complete solid.

Figure 3:
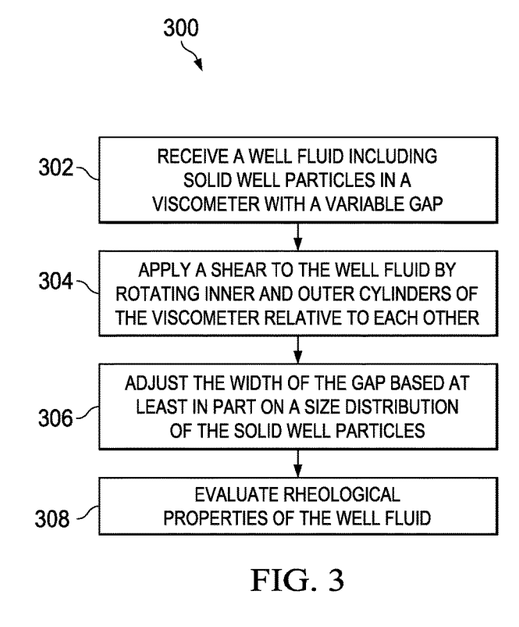
FIG. 3 is a flowchart of an example process for evaluating rheological properties of a well fluid using the variable diameter viscometer.

FIG. 3 is a flowchart of an example process 300 for evaluating rheological properties of a well fluid using the variable diameter viscometer 108. The process 300 can be implemented at the well site on well fluid, e.g., drilling fluid or production fluid, flowing out of the wellbore 102. For example, a continuous stream of drilling fluid can be transported from the well head 106 to the viscometer 108 as the drilling fluid exits the wellbore 102. A sample of the drilling fluid (e.g., a volume of the drilling fluid) can flow through the viscometer 108 for a duration sufficient to evaluate the rheological properties of the drilling fluid. Subsequently, the drilling fluid can exit the viscometer 208. Thus, the viscometer 208 continuously evaluates different samples of the drilling fluid over time. The volume fraction of solid well particles, e.g., drilling cuttings, debris, or other solid well particles, in the drilling fluid can change over time. Thus, the different samples of drilling fluid that flow through and are evaluated by the viscometer 208 may or may not include solid well particles, and, consequently, can have different apparent viscosities. The viscometer 108 can be operated to determine the different viscosities of the different samples continuously and without needing to be stopped to replace viscometer parts to vary the width of the gap 208.

At 302, a well fluid including solid well particles is received in a viscometer that includes a first portion and a second portion positioned adjacent the first portion to form a gap between the first portion and the second portion. For example, a sample of the drilling fluid that includes the drilling cuttings is received at the viscometer 108 from the wellbore 102 through tubing such as that shown in FIG. 1. At 304, a shear is applied to the well fluid in the gap 208 by moving the first portion and the second portion relative to each other. For example, the controller 110 provides input to rotate the inner cylinder 204 at a specified speed that corresponds to a specified shear rate. In response, the inner cylinder 204 rotates at the specified speed resulting in shear being applied to the well fluid in the gap 208.

Because the well fluid includes solid well particles, e.g., drilling cuttings or other well particles, the gap can get plugged resulting in an increase in the pressure in the gap or causing the viscometer to go off-scale, or both. In response, at 306, the width of the gap between the two portions can be adjusted based, at least in part, on a size distribution of the solid well particles in the well fluid. For example, the controller 110 can inflate or deflate the inflatable membrane 206 to adjust the width of the gap 208. In some implementations, the controller 110 can determine an increase in the pressure in the gap 208, and, responsively, provide input to gradually decrease the pressure in the inflatable membrane 206. As the pressure in the membrane 206 decreases, the membrane 206 deflates resulting in a widening of and a decrease in the pressure in the gap 208. In response, a rotational speed of the inner cylinder 204 increases to the speed specified at 302 and the controller 110 can then cease to provide input to further decrease the pressure in the inflatable membrane 206. The sample of drilling fluid that caused the gap 208 plugged can then exit the viscometer 208.

The next sample of drilling fluid that flows into the gap can have fewer solid well particles relative to the previous sample. The width of the gap can be too high or the pressure in the gap can be too low (or both) to apply the shear to the sample of the drilling fluid at the relative speed of the moving portions. In response, the controller 110 can provide input to gradually increase the pressure in the inflatable membrane 206. As the pressure in the membrane 206 increases, the membrane 206 inflates resulting in a shortening of the gap. In response, for example, a rotational speed of the inner cylinder 204 decreases to the speed specified at 302 and the controller 110 can then cease to provide input to further increase the pressure in the inflatable membrane 206.

In this manner, the controller 110 can continuously and in real-time control the width of the gap 208 to maintain the relative speed of the moving portions, e.g., the rotational speed of the inner cylinder 204, so that a constant shear rate is applied to different samples of the drilling fluid that flow through the viscometer 108. To control the width of the gap 208 in real-time means to adjust the width of the gap 208 in response to the relative speed of the moving portions, e.g., a rotational speed of the inner cylinder 204, or a pressure in the gap 208 (or both) by adjusting the pressure in the inflatable membrane 206 as immediately as allowed by the processing circuitry or the computer system implemented by the controller 110.

At 308, rheological properties of the well fluid are evaluated. For example, by applying a constant shear rate to different samples of drilling fluid that have different volume fractions of solid well particles, the controller 110 can evaluate different rheological properties of the drilling fluid. For example, by measuring a shear stress on the different samples of the drilling fluid, the controller 110 can determine different viscosities of the different samples. From the different viscosities, the controller 110 can determine a viscosity profile for the drilling fluid that flowed out of the wellbore 102.

In another example, the controller 110 can determine a volume fraction of the solid well particles in the well fluid. To do so, the controller 110 can implement the Thomas equation or other volume fraction equation relationships. The Thomas model is an improvement of the Einstein equation since it allows for much higher solids volume fraction. Furthermore, it provides the mathematics to deal with particle to particle interactions increasing viscosity and ultimately at very high volume fractions, viscosity increase to effectively a solid mixture. The Thomas model (2) is shown in Equation (1):

$$U^* = 1 + 2.5\phi + A\phi^2 + B \exp^{C\phi} \quad \text{(Equation 1)}$$

In Equation (1), $$U^* = \frac{U_f}{U_0}.$$

Further, $U_f$ is final viscosity and $U_0$ is initial viscosity. $\phi$ is the solid volume fraction which can range between 0 and 1, and A, B and C are empirical constants. Thus, by comparing rheology with and without cuttings the volume fraction can be estimated using Equation (1) and the empirical constants A, B, and C. The constants can be determined using known volume fraction fluids.

Alternatively or in addition, the controller 110 can determine the volume fraction from the viscosity measured as described above. In some implementations, the controller 110 can determine the solid volume fraction based on a change in the geometry of the inflatable membrane 206. For example, the controller 110 can set a large width of the gap 208. As the sample of drilling fluid with drilling cuttings is received in the gap 208, the controller 110 can gradually increase the pressure in the inflatable membrane 206 causing the width of the gap 208 to gradually decrease. When a surface of the membrane 206 contacts some of the drilling cuttings, the geometry of the membrane 206 can deform. Further increase in the pressure in the inflatable membrane 206 can result in further deformation of the geometry of the membrane 206. The controller 110 can determine a volume of the drilling cuttings in the sample based, in part, on factors including a width of the gap 208 when the membrane 206 began to deform, a quantity of deformation of the membrane 206, a rate at which the pressure in the membrane 206 was varied, combinations of them, or other factors.

In the examples described above, a constant shear was applied to different samples of drilling fluids. In some implementations, the controller 110 can apply different shear rates to the same sample of drilling fluid to determine the viscosity or the solid volume fraction (or both) of the sample. For example, the controller 110 can provide input to rotate the inner cylinder 302 to apply a first shear to a sample of the drilling fluid that may or may not include drilling cuttings. Subsequently, the controller 110 can provide input to apply a second shear to the same sample of the drilling fluid. To apply the two different shears, the controller 110 can adjust the width of the gap 208 or adjust a rotational speed of the inner cylinder 204 or both. The controller 110 can measure shear stresses responsive to the two shears, and determine a first viscosity and a second viscosity that correspond to the first shear and the second shear, respectively. From the two viscosities, the controller 110 can determine a volume fraction of the solid well particles in the well fluid.

Figure 4:
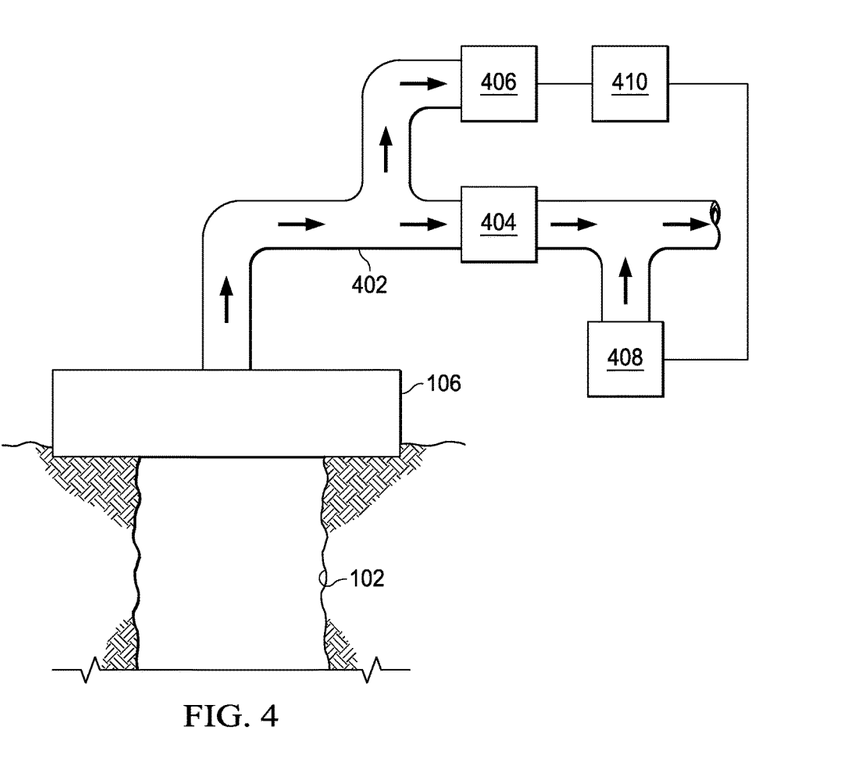
FIG. 4 is a schematic diagram of the well system implementing the variable diameter viscometer and another viscometer.

FIG. 4 is a schematic diagram of the well system implementing a variable diameter viscometer and another viscometer. In some implementations, the drilling fluid laden with the drilling cuttings can flow out of the wellbore 102 and into tubing 402 connected to the well head 106 at the surface. The tubing 102 can transport the drilling fluid laden with the drilling cuttings toward a filter 404, e.g., a shaker, which can remove the drilling cuttings from the drilling fluid. A variable diameter viscometer 406, which is substantially similar to the viscometer 208 described above, can receive the drilling fluid before the drilling cuttings are screened from the drilling fluid. In some implementations, the viscometer 406 can be arranged in parallel with the filter 404, as shown in FIG. 4. Alternatively, the viscometer 406 can be arranged in series with the filter 404. The drilling fluid that has been filtered by the filter 404 to remove the drilling cuttings can flow to a second viscometer 408, which can be a viscometer that is substantially similar to the viscometer 208 described above or any viscometer. The controller 410 can be connected to the viscometer 406 and the viscometer 408, and can be configured to provide inputs to operate both viscometers.

Different samples of the drilling fluid can flow to the viscometer 406. The controller 410 can determine the viscosities of the different samples of the drilling fluid that flow through the viscometer 406 using techniques similar to those described above with reference to controller 110. The drilling fluid can then be filtered by the filter 404. Different samples of the filtered drilling fluid can flow to the viscometer 408. The controller 410 can operate the viscometer 408 to determine the viscosities of the different samples from which the drilling cuttings have filtered. Some of the different viscosities determined using the viscometer 406 can be different from some of the different viscosities determined using the viscometer 406 due to removal of the drilling cuttings from the samples. The controller 410 can determine a solid volume fraction of the drilling cuttings in the different samples based, in part, on the different viscosities determined using the two viscometers.

The example techniques described above can be implemented at different temperatures or pressures or both. As described above, different samples of fluids can be evaluated at the same shear rates or the same sample of fluid can be evaluated at different shear rates or combinations of them.

Certain aspects of the subject matter described here are implemented as a method. A well fluid including solid well particles is received in a gap formed between a first portion and a second portion of a viscometer. A width of the gap is adjustable during operation of the viscometer. Rheological properties of the well fluid can be evaluated by applying a shear to the well fluid in the gap by moving the first portion and the second portion relative to each other, and by adjusting the width of the gap between the first portion and the second portion based, at least in part, on a size distribution of the solid well particles in the well fluid.

This, and other aspects, can include one or more of the following features. The first portion and the second portion can include an outer portion and an inner portion, respectively. The inner portion can be encompassed by the outer portion. The outer portion and the inner portion can include an outer cylinder and an inner cylinder, respectively. The inner cylinder can be positioned co-axially within the outer cylinder. The viscometer can include an inflatable membrane to adjust the width of the gap. The width of the gap can be adjusted during operation of the co-axial viscometer by applying a pressure to the inflatable membrane. The viscometer can be calibrated to determine a relationship between the width of the gap and the pressure applied to the inflatable membrane. To calibrate the viscometer, a relationship can be determined between multiple widths of the gap and multiple corresponding pressures applied to the inflatable membrane. Evaluating the rheological properties of the well fluid can include determining a volume fraction of the solid well particles in the well fluid. To determine the volume fraction of the solid well particles in the well fluid, the width of the gap can be increased to a size that is greater than the size of the solid well particles. The well fluid with the solid well particles can be flowed into the well gap. The width of the gap can be decreased over time. A change in a geometry of the inflatable membrane in response to the membrane contacting the solid well particles can be determined. The width of the gap at which the geometry of the inflatable membrane changed is identified. The shear can be a first shear. To evaluate the rheological properties of the well fluid, a second shear can be applied to the well fluid without the solid well particles. A first viscosity of the well fluid in response to the first shear can be determined. A second viscosity of the well fluid in response to the second shear can be determined. A volume fraction of the solid well particles in the well fluid based, in part, on the first viscosity and the second viscosity can be determined. In response to applying the shear, it can be determined that the pressure in the gap increases above a threshold pressure. The width of the gap can be adjusted to decrease the pressure below the threshold pressure.

Certain aspects of the subject matter described here can be implemented as a viscometer. The viscometer includes a first portion and a second portion positioned adjacent the first portion to form a gap between the first portion and the second portion. The first portion and the second portion can move relative to each other to apply shear to a fluid received in the gap. A controller is connected either to the first portion or the second portion to adjust a width of the gap while the first portion and the second portion move relative to each other.

This, and other aspects, can include one or more of the following features. The first portion and the second portion can include an outer portion and an inner portion, respectively. The inner portion can be encompassed by the outer portion. The outer portion and the inner portion can include an outer cylinder and an inner cylinder, respectively. The inner cylinder can be positioned co-axially within the outer cylinder. An inflatable membrane can be connected to the controller. The controller can adjust a pressure in the inflatable membrane to adjust the width of the gap. The viscometer can include a calibration sensor can determine a relationship between the width of the gap and the pressure in the inflatable membrane. The calibration sensor can include a mechanical sensor. The inflatable membrane can be attached to the outer cylinder. The inflatable membrane can be positioned inside the outer cylinder.

Certain aspects of the subject matter described here can be implemented as a method. A well fluid including solid well particles is received in a gap formed between a first portion and a second portion of a viscometer. A width of the gap is adjustable during operation of the viscometer. A shear is applied to the well fluid in the gap by moving the first portion relative to the second portion. The width of the gap is adjusted based, at least in part, on a size distribution of the solid well particles in the well fluid. Rheological properties of the well fluid are evaluated in response to applying the shear and adjusting the width.

This, and other aspects, can include one or more of the following features. The first portion and the second portion can include an outer portion and an inner portion, respectively. The inner portion can be encompassed by the outer portion. The outer portion and the inner portion can include an outer cylinder and an inner cylinder, respectively. The inner cylinder can be positioned co-axially within the outer cylinder. The viscometer can include an inflatable membrane to adjust the width of the gap. To adjust the width of the gap during operation of the co-axial viscometer, a pressure can be applied to the inflatable membrane.

A number of implementations of the subject matter have been described. Nevertheless, it will be understood that various modifications may be made without departing from the spirit and scope of the disclosure. Accordingly, other implementations are within the scope of the following claims.

What is claimed is:

1. A method comprising:
   receiving a well fluid comprising solid well particles in a gap formed between a first portion and a second portion of a viscometer wherein a width of the gap is adjustable during operation of the viscometer; and
   evaluating rheological properties of the well fluid by:
      applying a shear to the well fluid in the gap by moving the first portion and the second portion relative to each other; and
      adjusting the width of the gap between the first portion and the second portion based, at least in part, on a size distribution of the solid well particles in the well fluid.

2. The method of claim 1, further comprising:
   in response to applying the shear, determining that the pressure in the gap increases above a threshold pressure; and
   adjusting the width of the gap to decrease the pressure below the threshold pressure.

3. The method of claim 1, wherein the first portion and the second portion comprise an outer portion and an inner portion, respectively, the inner portion encompassed by the outer portion.

4. The method of claim 3, wherein the outer portion and the inner portion comprise an outer cylinder and an inner cylinder, respectively, the inner cylinder positioned co-axially within the outer cylinder.

5. The method of claim 1, wherein the viscometer comprises an inflatable membrane to adjust the width of the gap, and wherein the method further comprises adjusting the width of the gap during operation of the viscometer by applying a pressure to the inflatable membrane.

6. The method of claim 5, wherein evaluating the rheological properties of the well fluid comprises determining a volume fraction of the solid well particles in the well fluid.

7. The method of claim 6, wherein determining the volume fraction of the solid well particles in the well fluid comprises:
   increasing the width of the gap to a size that is greater than the size of the solid well particles;
   flowing the well fluid with the solid well particles into the gap;
   decreasing the width of the gap over time;
   determining a change in a geometry of the inflatable membrane in response to the membrane contacting the solid well particles; and
   identifying the width of the gap at which the geometry of the inflatable membrane changed.

8. The method of claim 5, wherein the shear is a first shear and wherein evaluating the rheological properties of the well fluid comprises applying a second shear to the well fluid without the solid well particles.

9. The method of claim 8, further comprising:
   determining a first viscosity of the well fluid in response to the first shear;
   determining a second viscosity of the well fluid in response to the second shear; and
   determining a volume fraction of the solid well particles in the well fluid based, in part, on the first viscosity and the second viscosity.

10. The method of claim 5, further comprising calibrating the viscometer to determine a relationship between the width of the gap and the pressure applied to the inflatable membrane.

11. The method of claim 10, wherein calibrating the viscometer comprises determining a relationship between a plurality of widths of the gap and a corresponding plurality of pressures applied to the inflatable membrane.

12. A viscometer comprising:

a first portion;

a second portion positioned adjacent the first portion to form a gap between the first portion and the second portion, the first portion and the second portion to move relative to each other to apply shear to a fluid comprising solid well paticles received in the gap; and a controller connected either to the first portion or the second portion to adjust a width of the gap while the first portion and the second portion move relative to each other, the controller configured to adjust the width based, at least in part, on a size distribution of the solid well particles in the fluid.

13. The viscometer of claim 12, wherein the first portion and the second portion comprise an outer portion and an inner portion, respectively, the inner portion encompassed by the outer portion.

14. The viscometer of claim 13, wherein the outer portion and the inner portion comprise an outer cylinder and an inner cylinder, respectively, the inner cylinder positioned co-axially within the outer cylinder.

15. The viscometer of claim 12, further comprising an inflatable membrane connected to the controller, wherein the controller to adjust a pressure in the inflatable membrane to adjust the width of the gap.

16. The viscometer of claim 15, wherein the inflatable membrane is attached to the first portion.

17. The viscometer of claim 15, further comprising a calibration sensor to determine a relationship between the width of the gap and the pressure in the inflatable membrane.

18. The viscometer of claim 17, wherein the calibration sensor comprises a mechanical sensor.

19. A method comprising:

receiving a well fluid comprising solid well particles in a gap formed between a first portion and a second portion of a viscometer, wherein a width of the gap is adjustable during operation of the viscometer;

applying a shear to the well fluid in the gap by moving the first portion relative to the second portion;

adjusting the width of the gap based, at least in part, on a size distribution of the solid well particles in the well fluid; and evaluating rheological properties of the well fluid in response to applying the shear and adjusting the width.

20. The method of claim 19, wherein the first portion and the second portion comprise an outer cylinder and an inner cylinder, respectively, the inner cylinder positioned co-axially within the outer cylinder, wherein the viscometer comprises an inflatable membrane to adjust the width of the gap, and wherein the method further comprises adjusting the width of the gap during operation of the viscometer by applying a pressure to the inflatable membrane.

* * * * *

UNITED STATES PATENT AND TRADEMARK OFFICE
CERTIFICATE OF CORRECTION

PATENT NO. : 10,241,019 B2
APPLICATION NO. : 15/322812
DATED : March 26, 2019
INVENTOR(S) : Dale E. Jamison, Kenneth Heidt Matthews and Andrew David Vos

Page 1 of 1

It is certified that error appears in the above-identified patent and that said Letters Patent is hereby corrected as shown below:

In the Claims

In Column 11, Line 16, Claim 12, after --solid well-- delete "paticles" and insert --particles--

Signed and Sealed this
Fourth Day of June, 2019

Andrei Iancu
*Director of the United States Patent and Trademark Office*